United States Patent
Murphy (12)

(10) Patent No.: US 6,366,207 B1
(45) Date of Patent: Apr. 2, 2002

(54) DEVICE FOR MODIFYING VEHICLE OPERATOR DRIVING BEHAVIOR

(76) Inventor: Michael Murphy, P.O. Box 908, Smyrna, TN (US) 37167-0908

( * ) Notice: Subject to any disclaimer, the term of this patent is extended or adjusted under 35 U.S.C. 154(b) by 0 days.

(21) Appl. No.: 09/497,692

(22) Filed: Feb. 4, 2000

(51) Int. Cl.[7] .............................................. G08B 23/00
(52) U.S. Cl. ..................... 340/576; 340/573.1; 340/540
(58) Field of Search ................................. 340/576, 575, 340/573.1, 540; 180/272

(56) References Cited

U.S. PATENT DOCUMENTS

| | | | |
|---|---|---|---|
| 3,856,991 A | * 12/1974 | Kirkland, Jr. et al. | 73/646 |
| 4,004,290 A | 1/1977 | Kobayashi et al. | 340/279 |
| 4,072,925 A | * 2/1978 | Yashima et al. | 340/461 |
| 4,219,800 A | 8/1980 | LeViness | 340/576 |
| 4,342,023 A | * 7/1982 | Tsunoda et al. | 340/460 |
| 4,706,072 A | 11/1987 | Ikeyama | 340/576 |
| 4,839,749 A | 6/1989 | Franklin | 360/12 |
| 4,987,403 A | 1/1991 | Apfel | 340/457 |
| 5,101,926 A | 4/1992 | Berman et al. | 180/272 |
| 5,300,925 A | * 4/1994 | Depfenhart | 340/676 |
| 5,465,079 A | 11/1995 | Bouchard et al. | 340/576 |
| 5,574,641 A | 11/1996 | Kawakami et al. | 340/576 |
| 5,717,606 A | 2/1998 | Hara et al. | 180/272 |
| 5,874,892 A | 2/1999 | Antonellis et al. | 340/438 |
| 6,060,989 A | * 5/2000 | Gehlot | 340/576 |
| 6,271,746 B1 | * 8/2001 | Lisiak et al. | 340/425.5 |

* cited by examiner

Primary Examiner—Daniel J. Wu
Assistant Examiner—Sihong Huang
(74) Attorney, Agent, or Firm—Shlesinger, Arkwright & Garvey LLP

(57) ABSTRACT

Device for monitoring and/or modifying vehicle operator behavior. The device is suited for reducing vehicle operator aggressive driving behavior which leads to increased anger and so-called "road rage", and includes a sensor mountable in a vehicle that detects a vehicle driving condition exceeding a preset vehicle driving condition. A signal is operatively associated with the sensor and provides a warning to a vehicle operator when the sensor detects a vehicle driving condition which exceeds a predetermined value. The signal to the driver is deactivated and stops providing the warning when the sensor detects the preset vehicle driving condition for greater than a predetermined period of time. The warning to the operator may be a caution such as "Easy, now" and "You can let it go". The device may provide. "positive strokes" to the operator when the operator has driven for a predetermined number of miles or length of time, for example, without engaging in any behavior(s) which exceeds predetermined values. The warnings and/or positive strokes may be audible signals or visual signals, for example.

35 Claims, 4 Drawing Sheets

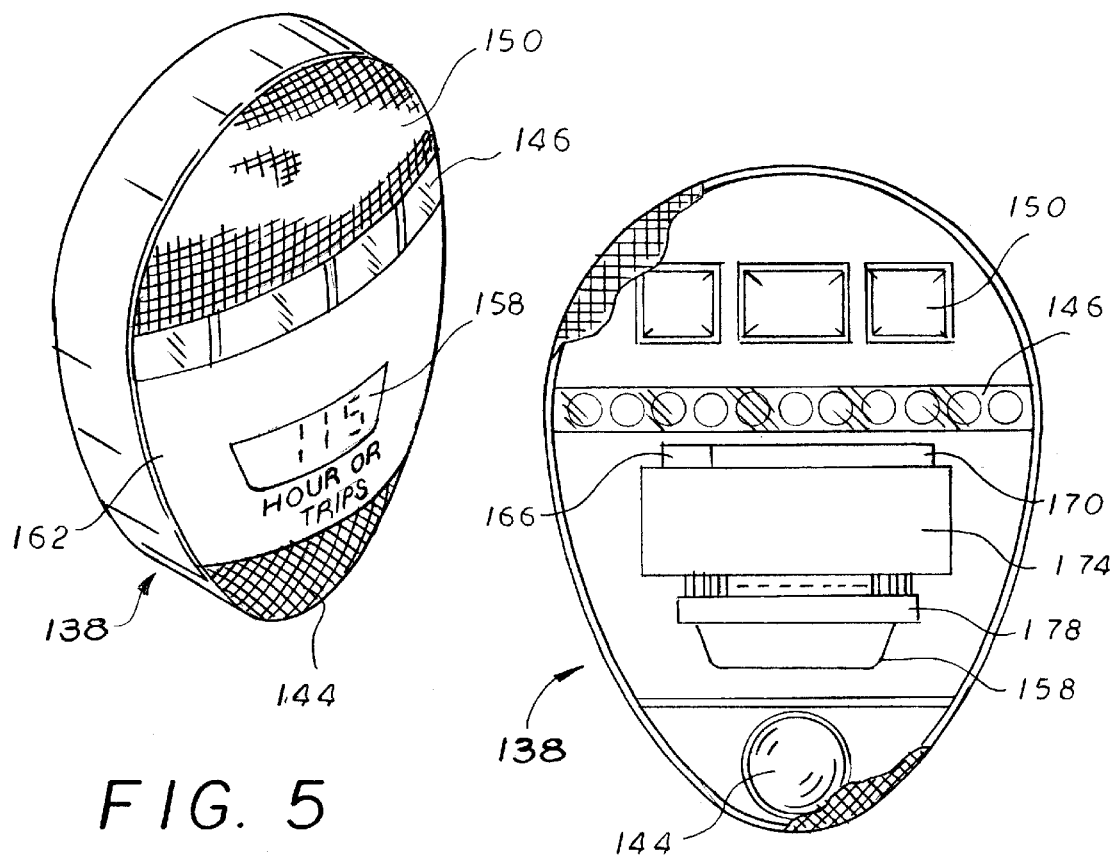
FIG. 5
FIG. 6
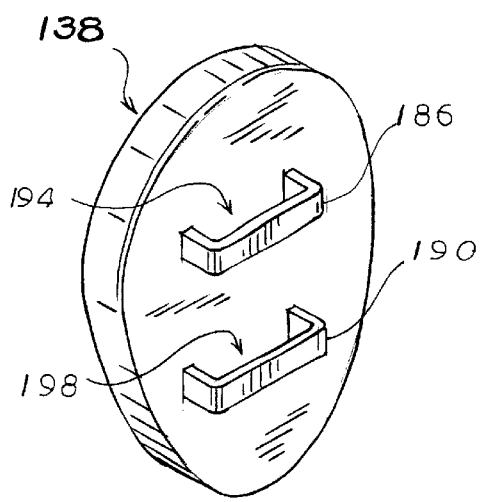
FIG. 7
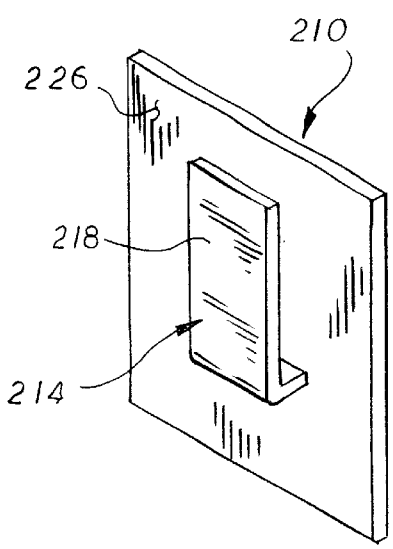
FIG. 8

DEVICE FOR MODIFYING VEHICLE OPERATOR DRIVING BEHAVIOR

FIELD OF THE INVENTION

This invention relates to a device for modifying human behavior. The invention is suited for modifying human behavior while operating vehicles, in the workplace and at home. The invention is likewise suited for reducing aggressive driving behavior, for example, for avoiding escalation of aggressive behaviors that lead to unsafe aggressive driving, commonly known as "road rage".

BACKGROUND OF THE INVENTION

Attempts have been made to modify human behavior by praising the behavior with compliments ("positive strokes") and/or by criticizing undesired behavior ("negative strokes").

Under most situations, it has been found that praising individual's attempts at or exhibiting desired behavior with positive strokes yields the desired behavioral change more quickly and for a longer-lasting period of time, if not permanently, than by criticizing the undesired behavior or providing "negative strokes". It has also been found that giving no strokes is more powerful than giving negative strokes.

In the field of automobiles, many vehicle operators have been angered by other vehicle operator's behavior or simply by road driving conditions, stop lights, and the like, since the days when vehicles became commonplace and rules of the road came about in the twentieth century.

It is known that under certain conditions, a segment of the vehicle driving population may become so annoyed by other's driving, or by circumstances beyond the operator's control, that the annoyed vehicle operator will engaged in non-standard, aggressive driving behavior and/or yelling, and the like.

If such aggressive driving behavior is not reduced in a timely fashion, the aggressive driving tends to escalate due to an ongoing exchange of negative strokes between, for example, two vehicle operators. Owing to the exchange of negative strokes, the aggressive driving tends to escalate, often to the point of so-called "road rage".

Typical negative strokes involved in driving include such acts as yelling, sudden braking, frequent braking, following too closely behind another operator's vehicle (i.e., so-called "tailgating"), honking the vehicle horn, gesturing, changing lanes with inadequate room for safely doing so (i.e., "cutting in and out of lanes"), speeding, and the like.

Although there have been prior attempts at monitoring or controlling driving behavior, no known attempts have been made to modify driver behavior by the use of positive strokes, and cautions about the manner in which the vehicle operator is driving, for example.

There are known devices which are for monitoring limited aspects of operator and vehicle driving data.

Known examples of prior art devices include U.S. Pat. No. 5,465,079 to Bouchard et al.; U.S. Pat. No. 4,219,800 to LeViness; U.S. Pat. No. 4,839,749 to Franklin; U.S. Pat. No. 4,987,403 to Apfel; U.S. Pat. No. 5,717,606 to Hara et al.; U.S. Pat. No. 5,874,892 to Antonellis et al.; U.S. Pat. No. 5,574,641 to Kawakami et al.; U.S. Pat. No. 5,101,926 to Berman et al.; U.S. Pat. No. 4,004,290 to Kobayashi et al.; and U.S. Pat. No. 4,706,072 to Ikeyama.

It can be seen that there is a need for a more versatile device, system, and method of monitoring driver behavior.

OBJECTS AND SUMMARY OF THE INVENTION

It is an object of the invention to overcome the drawbacks of the prior art devices.

It is further object of the invention to monitor vehicle operator data and to provide feedback to the vehicle operator and/or to another person and/or to a database.

It is another object of the invention to provide a vehicle operator behavior modification device which is more effective at achieving the desired result than known devices.

Yet another object of the invention is to provide a vehicle operator behavior modification device which provides feedback directly to the vehicle operator at the time the monitored behavior occurs.

Yet another object of the invention is to provide a vehicle operator behavior modification device which uses positive strokes to achieve the desired modification of behavior, and to remove all strokes should feedback be ignored.

In summary, the invention is directed to a device for modifying vehicle operator driving behavior that includes a sensor mountable in a vehicle. The sensor detects a vehicle driving condition which differs from a preset driving condition. A signal is operatively associated with the sensor and provides a notice to the vehicle operator when the sensor detects a vehicle driving condition which differs from a predetermined value. The signal is deactivated and stops providing the notice when the sensor detects the vehicle preset driving condition for a period of time which differs from a predetermined period of time.

The use of relative terms such as left, right, up and down is for convenience only and is not intended to be limiting.

For convenience, the vehicle operator modification device according to the invention is often referred to as a vehicle operator aggressive behavior reduction device.

BRIEF DESCRIPTION OF THE DRAWINGS

FIG. 5 is a perspective view of another preferred embodiment of a vehicle operator behavior modification device according to the invention;

FIG. 6 is front view of the embodiment of FIG. 5 with its face plate removed;

FIG. 7 is a rear perspective view of the preferred embodiment of FIG. 5; and

FIG. 8 is a perspective view of an attachment plate which may be used to secure the preferred embodiment of FIG. 5 to a vehicle.

DETAILED DESCRIPTION OF THE INVENTION

Figure 1:
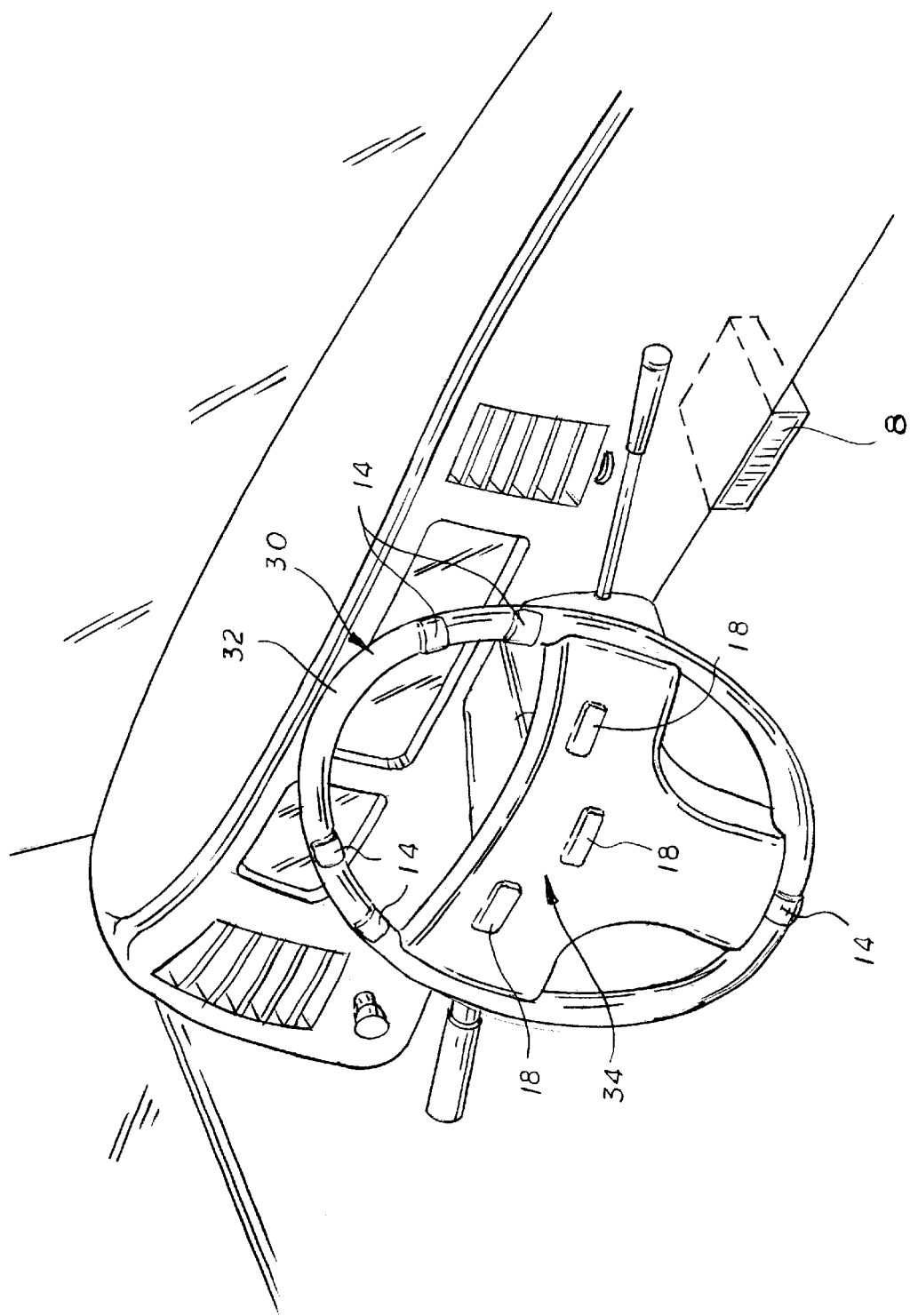
FIG. 1 shows a first preferred embodiment of the vehicle operator behavior modification device, as installed in a vehicle.
Figure 2:
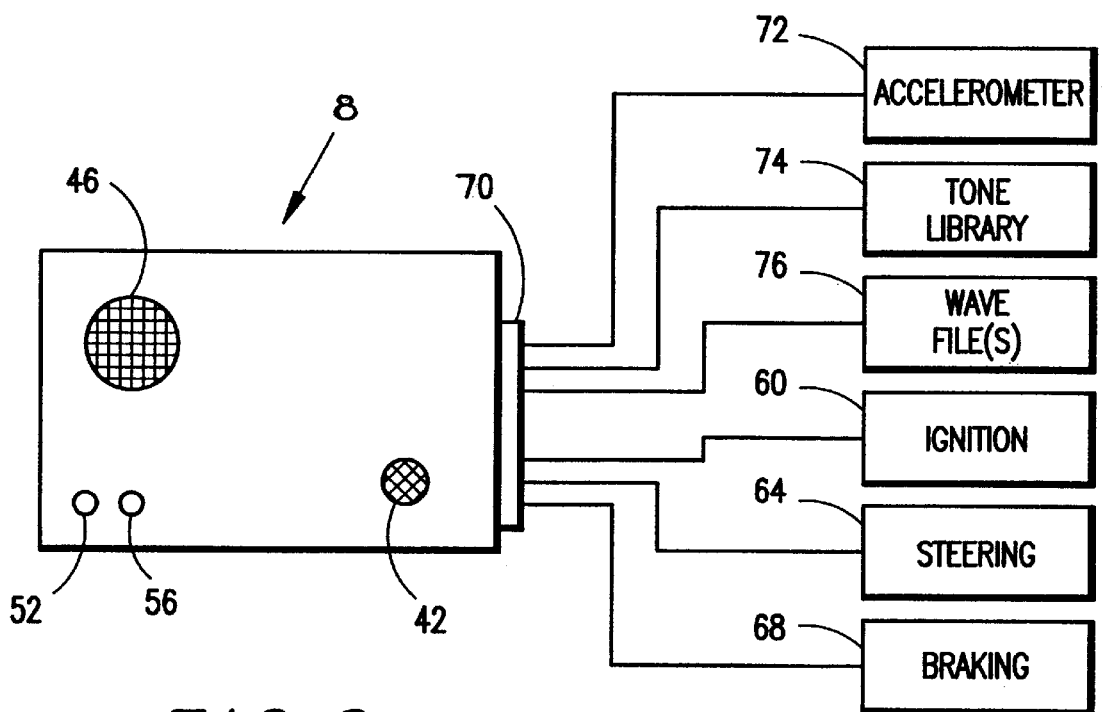
FIG. 2 is a somewhat schematic representation of the preferred embodiment of FIG. 1.

Turning to the drawings, FIGS. 1 and 2 illustrate a first preferred embodiment of a vehicle operator behavior modification device 8 according to the invention.

For convenience, behavior modification device 8 will be described as an exemplary embodiment of an aggressive behavior reduction device for use in cases where aggressive behavior on the part of the vehicle operator is sought to be reduced or eliminated.

Behavior modification device 8 may be installed adjacent the dashboard of a passenger car, as illustrated.

One or more steering wheel gripping pressure sensors 14 for measuring the amount of pressure exerted thereon and one or more horn usage pressure sensors 18 may be provided at respective location(s) on a steering wheel assembly 30.

Typically, steering gripping pressure sensors 14 will be provided on a steering wheel region 32 of steering wheel assembly 30. Likewise, horn usage pressure sensor 18 may be provided at one or more locations on or adjacent a horn region 34 of steering wheel assembly 30.

A microphone 42 for picking up sounds for an associated sensor for measuring the intensity of sounds within the vehicle (e.g., the sound pressure level within the vehicle) may be provided on behavior modification device 8.

A speaker or signal 46 may likewise be provided on behavior modification device 8 for providing a notice or signal to a vehicle operator. The type and duration of the notice may be dictated by the type, intensity, duration, and number of inputs, such as the pressure sensors 14 and 18 described above, and additional inputs described below.

One or more visual indicators 52 and 56 may provide visual notice(s) to a vehicle operator.

In FIG. 2, two (2) visual signals are provided, one of the signals 52 being a blue LED (i.e., light-emitting diode) and visual signal 56 being an amber LED. Other colors may be used.

Both steering gripping pressure sensor 14 and horn usage pressure sensor 18 detect respective vehicle driving conditions which may differ from respective preset vehicle driving conditions.

In the case of steering gripping pressure sensor 14, the vehicle driving condition which differs from a preset vehicle driving condition may be a steering gripping pressure which exceeds a preset pressure; e.g. a preset pressure corresponding to a "normal" steering gripping pressure. That normal gripping pressure may be a factory-preset value determined by the expected normal gripping pressure of a standard population of vehicle operators; or, the preset steering gripping pressure may be set by the installer or set by the vehicle operator herself under normal driving conditions. Furthermore, it is contemplated that behavior modification device 8 itself will gather steering gripping pressure data by continuously monitoring steering gripping pressure or by randomly sampling steering gripping pressure of a particular individual, for example, when the vehicle is being operated in a normal fashion.

In the case where device 8 is used to detect and reduce aggressive driving, when the preset pressure is exceeded, such as by the operator's gripping the steering wheel harder than usual, then a signal is sent to emit a notice to the operator, as will be described in detail below.

In the case where device 8 is set to detect inattentiveness or sleepiness, for example, by which the operator grips the steering wheel with less than a predetermined amount of pressure, then a notice would be emitted when less than a predetermined pressure is applied for greater than a predetermined amount of time, for example.

In an analogous fashion, the preset pressure level corresponding to a preset or baseline pressure to which the pressure detected by horn usage pressure sensor 18 is compared may be factory set, installer set, operator set, or actively set and continually monitored for change, as needed, based on continuous sampling of pressure data sampled by behavior modification device 8 itself.

It is further contemplated that the preset pressure may be actively varied based on road conditions, vehicle driving conditions, and/or other data actively measured by additional sensors of the type outlined below.

FIG. 2 illustrates the manner in which additional inputs can be directed to behavior modification device 8.

For example, microphone 42 may be provided to detect and transmit vehicle interior sound levels. The detected sound pressure levels may be compared to baseline or preset sound pressure levels by device 8 and one or more signal devices may provide respective notices or warnings to the vehicle operator when the measured sound pressure level exceeds preset sound pressure levels. As with the other sensors, the preset levels may be factory installed, installer installed, consumer installed, or may be continuously changing thanks to the continuous monitoring or random sampling of sound pressure levels under standard operating conditions.

A speaker 46 is actively coupled to the remainder of behavior modification device 8. Speaker 46 emits an audible warning or notice when one or more of the measured vehicle inputs so dictates, based on calculations performed by the computer or computer chips provided in behavior modification device 8.

Visual outputs or signals may be provided in the form of lights or LEDs 52 and 56. Visual signal 52 may be a blue LED and visual signal 56 may be a yellow or amber LED (or other colors).

Blue LED 52 may be lighted when the vehicle operator's behavior and/or the operation of the vehicle is within the predetermined behavior and operating ranges. Quite simply, blue LED 52 may indicate that device 8 is ON and the vehicle is being operated in the desired fashion.

Amber LED 56 may be lighted when one or more of the measured driver behavior or vehicle operating characteristics deviate sufficiently from the desired, preset condition that a notice or warning to the vehicle operator is warranted.

For example, when the vehicle operator is in a stressful situation, and driving aggressively, gripping or clinching steering wheel region 32, and hence, one or more of steering gripping pressure sensors 14 with a greater than preset pressure, the unillustrated computer/computer chip will cause the amber LED 56 to light. The speaker 46 may be used in addition to or instead of visual warning amber LED 56.

The audible warning emitted by speaker 46 may be in the form of a tone or in the form of a voice message to the driver, such as "Easy, now" and "You can let it go", for example.

In the case where a tone is emitted by speaker 46, one or more tones, such as a bell, a chime, a whistle, or other tone may be stored in a tone library 74 stored on the computer or the computer chip found in behavior modification device 8.

Similarly, the emitted phrase(s) may be stored in a wave file(s) 76 stored on the computer of behavior modification device 8.

To avoid aggravating aggressive driving, the audible tone or phrase will typically be halted if the aggressive driving which prompted the emission of the audible notice/warning continues for more than a few seconds.

The use of an audible tone or phrase is termed an intervention. The purpose of the intervention is to briefly distract the driver engaged in aggressive driving behavior to keep the driver from escalating the aggressive behavior and to remind the driver that he/she has a choice to either continue or to stop the aggressive behavior. The notice intervention is discontinued if ignored so as to not serve as a stroke which could make the operator angrier, or to reinforce the aggressive behavior.

An accelerometer may be provided to measure the acceleration or deceleration of the vehicle. By measuring the acceleration (i.e., the rate of change of vehicle speed) and by comparing the acceleration to preset normal acceleration/deceleration values on the computer chip of behavior modification device 8, yet another measure of aggressive driving behavior is provided. Sudden accelerations and decelerations (such decelerations being experienced in rapid braking, for example) may indicate aggressive driving such as found in tailgating (i.e., following the vehicle in front too closely) and rapid risky lane change behavior such as cutting in and out of traffic.

It is also contemplated to measure jerk (i.e., the rate of change of acceleration) as yet another determinant of aggressive driving behavior for which intervention is warranted.

An ignition input 60 may be used to determine whether the vehicle is in an ON or OFF mode or condition.

For some applications, it is contemplated that if a vehicle operator ignores a notice or warning emitted by one or both of amber LED 52 and speaker 46, then behavior modification device 8 will shut down until after the vehicle has gone through a vehicle OFF condition followed by a vehicle ON condition. In other words, the behavior modification device 8 will shut itself off until the vehicle been turned off and on, with presumably enough time between the trip in which aggressive driving took place and the next trip so as to allow the vehicle operator to settle down or regain his or her composure.

A clock may likewise be provided on the computer chip so that the vehicle OFF condition will have to be for a sufficiently long period of time so as to allow the vehicle operator to regain his composure.

Such a clock or an additional clock may be used for determining when a positive or acknowledging phrase "for the past twenty minutes you have been driving very well" is emitted.

The use of a clock is described in further detail below.

A steering input sensor 64 is provided that monitors one or both of steering gripping pressure, such as measured by pressure sensor 14 on steering wheel region 32 or measures steering angle input data to determine whether the steering wheel is moved back and forth to turn the car left and right in a greater than usual manner, for example. The steering input sensor 64 may be used for measuring the rate of change of the steering wheel angle, such as may be indicative of rapid lane changing.

A braking input 68 may be provided for collecting and inputting data from brake usage to the computer chip on device 8 so as to again help determine by itself or in conjunction with other inputs, whether the vehicle operating condition or vehicle operator behavior deviates sufficiently from preset conditions as to warrant emitting a visual or audible notice or both.

A connector block 70 may be provided on behavior modification device 8. Connector block or interface 70 may be provided with one or more connector sites, such as standard electrical connectors, to which the output wires, for example, of the various sensors may be attached.

Figure 3:
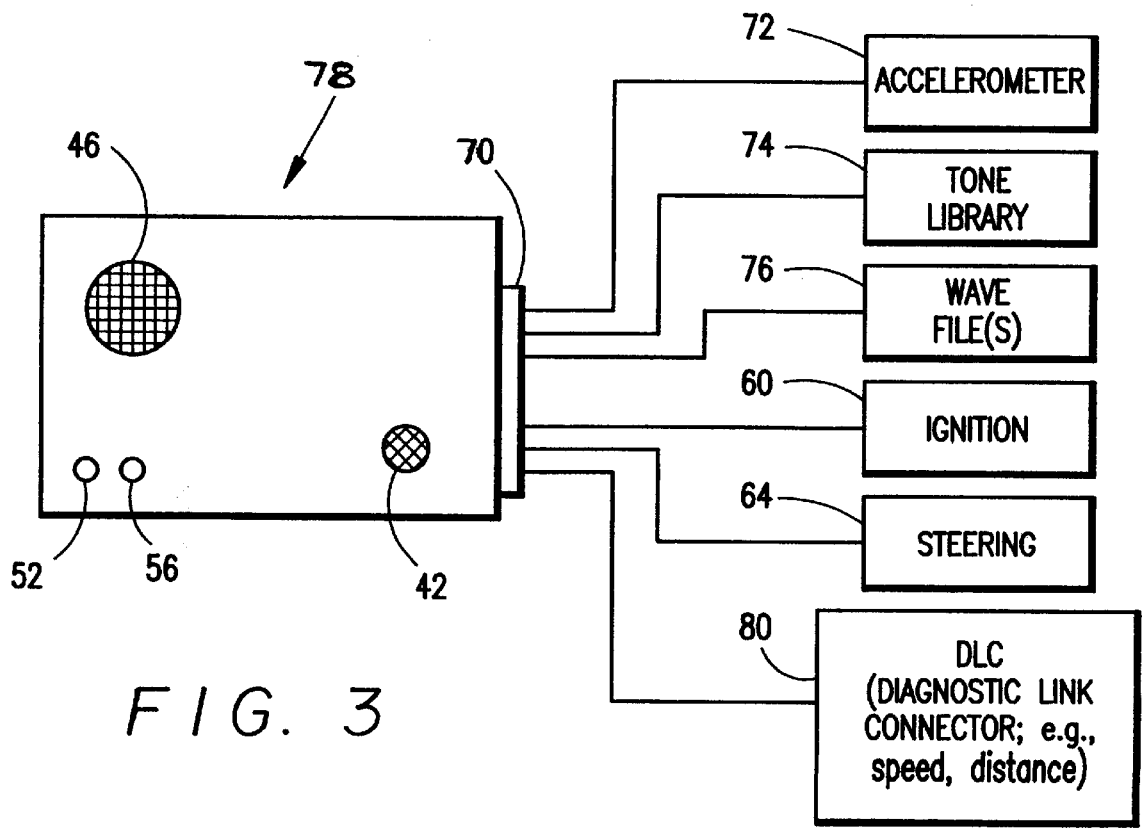
FIG. 3 shows another preferred embodiment of the vehicle operator behavior modification device according to the invention.

FIG. 3 illustrates a further another preferred embodiment of a behavior modification device 78 according to the invention.

Behavior modification device 78 has many inputs and outputs in common with the behavior modification device 8 of the preferred embodiments of FIGS. 1 and 2 of the invention.

In addition to the features of the preferred embodiment of FIGS. 1 and 2, behavior modification device 78 of FIG. 3 may be provided with a diagnostic link connector (DLC) 80. Diagnostic link connector (DLC) 80 may be used for sensing and measuring additional inputs, such as vehicle speed, distance traveled, engine rpm (revolutions per minute), vehicle jerk (i.e., rate of change of acceleration) other engine and vehicle data, date, time, and the like.

Thus, for example, in the preferred embodiment of FIG. 3 non-standard or abnormal driving behavior can be measured using an even greater number of inputs than in the preferred embodiment of FIGS. 1 and 2.

Figure 4:
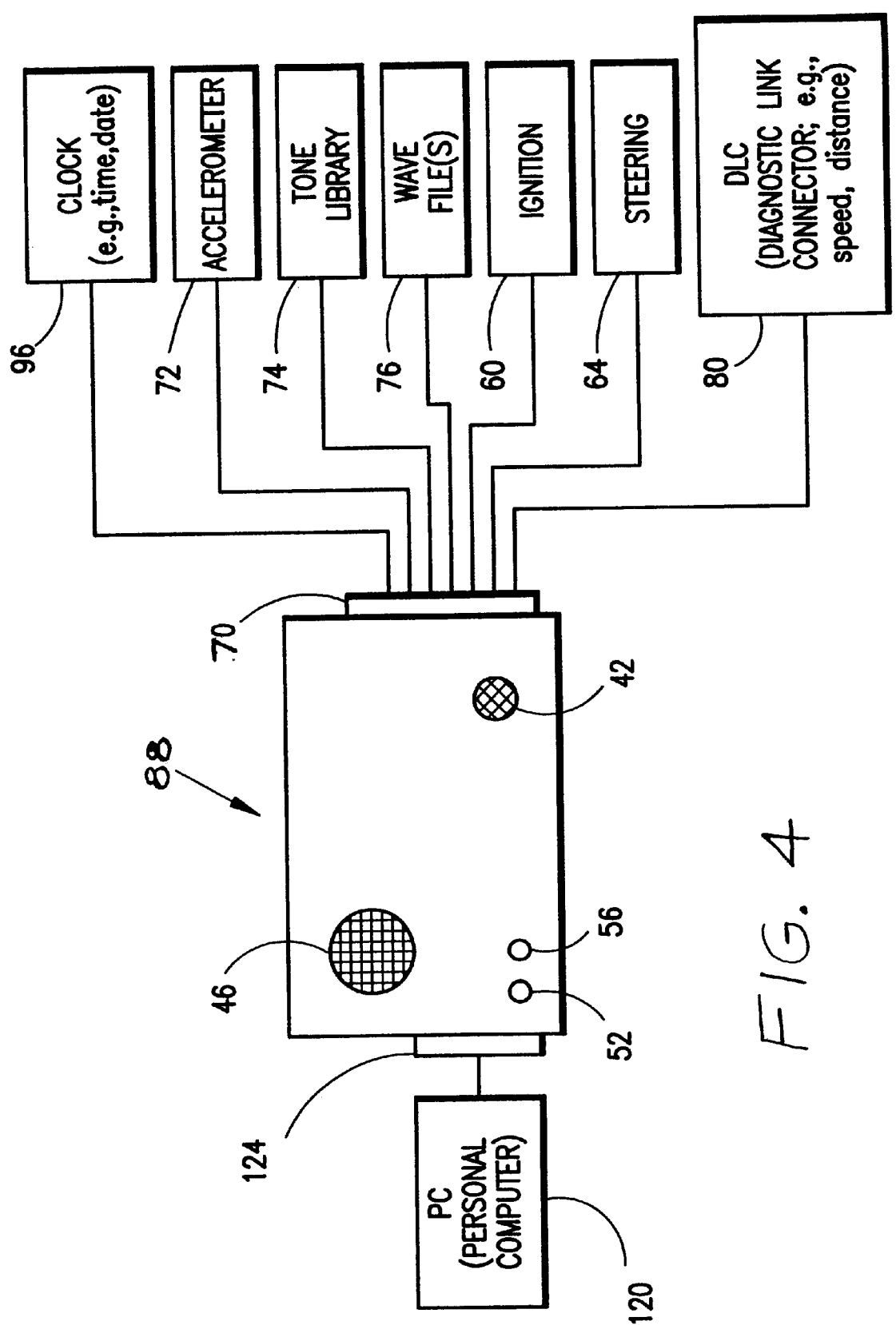
FIG. 4 illustrates a still further preferred embodiment of a vehicle operator behavior modification device according to the invention.

FIG. 4 illustrates another preferred embodiment of a behavior modification device 88 according to the invention.

Behavior modification device 88 may be provided with the inputs and outputs, as in the other preferred embodiments of the invention, along with a personal computer (PC) 120, for example. A PC interface 124 may be provided for linking behavior modification device 88 and PC 120.

PC 120 may be hooked up to interface 124 while the vehicle is in use, or may be hooked up when the vehicle is stopped so that information collected by behavior modification device 88 during the course of a trip or trips may be downloaded into PC 120.

In that manner, the driver may be given substantially instantaneous feedback as to her driving behavior and the vehicle operation data. Likewise, an employer, parent, or public servant may download the data for analysis. By the use of PC 120, a software report may be provided.

It is to be understood that PC 120 includes any of a variety of computing devices including, but not limited to, portable, so-called laptop computers and somewhat miniaturized computers of the type that fit into one's suit jacket pocket, pants pocket, pocketbook, or purse, for example.

FIGS. 5–8 illustrate another preferred embodiment of a behavior modification device 138 according to the invention.

Behavior modification device 138 is particularly suited for portable use. It is likewise suited for installation by the vehicle operator himself without the use of tools. Behavior modification device 138 may include a microphone 144 for picking up or sensing sounds within the vehicle being monitored. One or more lights or LEDs 146 may be provided. Lights 146 may be used to indicate device 138 ON and OFF conditions and/or serve as visual outputs responsive to the sensor inputs, analogous to the use of lights as described above, and as will be described in detail below.

A speaker 150 may be provided for emitting a reminder tone or message responsive to sensor inputs.

A trip meter and/or clock may be provided that tracks the number of hours driven during one particular roadtrip or driven cumulatively over multiple roadtrips. In addition to or instead of measuring elapsed time or hours, the tripmeter may record and visually display the number of miles driven or trips taken since behavior modification device 138 emitted a visual or audible notice/warning responsive to driver behavior or driven vehicle characteristic(s) that deviated from the predetermined range of measured values.

A faceplate 162 may be provided to cover the components and maintain them dust-free for example. FIG. 6 shows portable device 138 with face plate 162 removed. A database 166 is shown adjacent to a microprocessor clock, a computer chip 174, and transducer 178.

Computer chip 174 may perform many of the calculations determined to be necessary for analyzing the signal sent from a sensor (e.g., illustrated microphone 144).

Database 166 typically will contain factory down-loaded software that will be used in conjunction with operations and input/outputs from chip 174 to determine the proper response based on decibel levels/sound pressure levels detected by microphone 144.

In the illustrated embodiment of FIGS. 5–8, the sound level or decibel level detected within the vehicle at microphone 144 is the sole input which determines whether or not an output cautionary tone or reminder voice is emitted through speaker 150.

It is contemplated that an accelerometer be used instead of or in addition to microphone 144 in portable device 138.

In the case where an accelerometer is used in conjunction with or instead of microphone 144, then a different database may be substituted for database 166 and/or different computer code may be downloaded into computer chip 174. It is often easier in a factory setting to switch one pre-programmed database 166 for another than to download computer code into computer chip 174.

FIG. 7 illustrates the rear of portable device 138. One or more female fasteners 186 and 190 may be provided on the back face of portable device 138. Female fasteners 186 and 190 define respective holes 194 and 198.

FIG. 8 shows an attachment plate 210 on which a male fastener 214 having an extension 218 is provided. As shown, extension 218 may extend along face 226. In use, attachment plate 210 may be secured to a surface inside the vehicle, such as on a portion of the dashboard, so that extension 218 extends upwardly. When behavior modification device 138 is to be attached, it is moved downwardly relative to extension 218 so that 218 passes first through hole 198 and then through hole 194. In that manner, device 138 is removably secured to attachment plate 210 which, in turn, has been secured to the vehicle. Device 138 may be removed when not in use, or may be moved from one vehicle to another, as the operator's need may dictate.

Attachment plate 210 may be secured to the vehicle by the use of standard fasteners, or by an adhesive, such as double-sided tape provided on the side of attachment plate 210 opposite to male fastener 214.

In use, one or more of the lights 146 may be on to indicate a vehicle ON condition, or none of the lights may be on. In the case where one or more of the light 146 are on during standard operating conditions, a sound inside the vehicle compartment, such as the yelling of an annoyed driver that exceeds a predetermined threshold will cause additional lights 146 or all lights 146 to light. The vehicle operator thus will be provided with a visual reminder or signal that her yelling exceeds what has been determined to be a normal voice level as programed into the computer chip 174 and/or database 166. Alternatively, some of lights 146 may be blue to indicate a device ON condition and, when the measured sound/voice level exceeds the predetermined level, the blue lights may be turned off and previously unlighted amber lights 146 may be turned on to serve a visual notice to the operator.

As in the other embodiments, speaker 150 may be used instead of or along with lights 146 to provide a vehicle operator with an audible notice or warning that his behavior exceeds standard expected behavior.

In this portable version, for example, lights 146 may first flash when the sound level has exceed the predetermined sound level, a tone may concurrently be emitted from speaker 150, and then a phrase of encouragement may follow, such as "Take it easy".

The tone and/or flash of lights are intended to briefly distract the driver in the case where the driver is engaged in aggressive behavior, for example.

It should be understood that in the case where two or more data inputs, such as the above-described sensors, are available in each of the devices, the deviation from the expected data values when two or more sensors deviate from the expected value may each be less than the value required for a single sensor to cause the behavior modification device to alert the driver that her behavior is outside the norm.

For example, in the case where sound/voice level and steering wheel gripping pressure are detected, if the driver yells sufficiently loudly, even though the steering wheel is not being gripped hard enough to, by itself, exceed the predetermined value, the yelling alone will cause the device to emit a notice/warning to the driver. And, even if neither the horn gripping pressure nor the sound/voice level exceeds a preset respective value sufficiently high to, by itself, activate the notice/warning, those two acts together (i.e., gripping pressure on the wheel and yelling) may collectively cause the notice/warning to be emitted.

It must be further appreciated that in the case where the values from three or more sensors are received and compared to preset values, then the thresholds required for causing the notice/warning to be emitted may be even lower than when only two particular sensors are being monitored and are outputting signals which exceed a preset signal.

Quite simply, various weighting factors come into play depending on the type of signal being monitored relative to the other signals being monitored.

In other words, a particular set of steering and braking inputs may cause a notice/warning signal to be emitted, while, in the case where only the acceleration/deceleration signals and steering usage signals deviate from preset values, the preset value for steering usage may differ when coupled with the accelerometer values than when the steering usage output values are coupled with braking output values.

This can be further appreciated by considering that as a practical matter, some drivers do not yell when they are angry. Rather, those drivers internalize their anger and grip the steering wheel harder. Other drivers do not yell, rather they grip the steering wheel hard and "pound" on the horn; i.e., strike the horn at a greater than preset pressure value.

The duration of the yelling, the horn usage, the steering wheel gripping pressure, and each of the other measured values may be measured. In that manner, "false alarms" (i.e., erroneous notices) are reduced. For example, the fine-tunning of the length of time required for yelling to activate the notice may be sufficiently short so as to preclude activation of the notice by a human sneezing inside the vehicle.

It is likewise contemplated that specific sequences of measured values, with or without weighting factors, will be used to determine whether a notice/warning will be given to the operator. For example, alternating braking, acceleration, braking, acceleration, each in sequence, even within normal values, may be used to trigger a notice.

The length of time between successive actions may likewise be factored in as a further weighting factor.

It is contemplated that any of the behavior modification devices according to the invention be used specifically to monitor aggressive driving and serve as aggressive driving or aggressive behavior reduction devices.

In that case, many, but not necessarily all, of the notices/warnings will be activated when the measured values exceed predetermined values.

It is further contemplated that the invention may be used in the workplace and the home, for example, for use in monitoring sound levels, for example, that exceed predetermined sound levels to encourages workers and home occupants to lower their voices, for example. Some pressure sensors could be installed on desks, and other locations where monitored people might exert pressure by pounding their desks.

In the portable version, for example, double-sided tape or other fasteners could be used for temporary or permanent installation instead of the illustrated male and female fasteners.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

What is claimed is:

1. A method of modifying vehicle operator driving behavior, the method comprising:
   a) providing a sensor mountable in a vehicle, the sensor detecting an aggressive vehicle driving condition which differs from a preset normal vehicle driving condition;
   b) providing a signal operatively associated with the sensor, the signal providing a notice to the vehicle operator when the sensor detects the aggressive vehicle driving condition which differs from the preset normal vehicle driving condition;
   c) deactivating the signal and stopping the notice when the sensor detects the preset normal vehicle driving condition for a period of time which differs from a predetermined period of time;
   d) deactivating the signal and stopping the notice when the sensor detects the aggressive vehicle driving condition for a further period of time which differs from a further predetermined period of time; and
   e) causing said step of deactivating the signal and stopping the notice to occur to stop the notice if the aggressive vehicle driving condition continues for greater than the further predetermined period of time, the further predetermined period of time being selected so as to not anger the vehicle operator by giving the vehicle operator a negative stroke.

2. A method as in claim 1, wherein:
   a) said step of deactivating the signal and stopping the notice stops the notice when the aggressive vehicle driving condition stops.

3. A method as in claim 2, wherein:
   a) the sensor provided in said step of providing a sensor includes at least two of an accelerometer, an engine rpm sensor, a speed sensor, a sound-actuated sensor, a brake-usage sensor, a horn-usage sensor, and a steering wheel-usage sensor; and
   b) the at least two sensors initiate the signal to provide a notice when each respective one of the at least two sensors detects a respective vehicle condition which exceeds a further predetermined value and which further predetermined value is less than or equal to a predetermined value corresponding to the preset normal vehicle driving condition.

4. A method as in claim 1, wherein:
   a) the sensor provided in said step of providing a sensor detects a vehicle driving condition which is less than or equal to the preset normal vehicle driving condition; and
   b) the said signal provided in said step of providing a signal provides a positive stroke to a vehicle operator when the sensor detects the vehicle driving condition which is less than or equal to the preset normal vehicle driving condition for more than a first predetermined period of time.

5. A method as in claim 4, wherein:
   a) the positive stroke is provided after the notice has been provided, when the aggressive vehicle driving condition which had exceeded the preset normal vehicle driving condition is reduced to or is less than the preset normal driving condition within a second predetermined period of time.

6. A method as in claim 4, wherein
   a) said positive stroke includes an audible phrase of encouragement.

7. A method as in claim 1, wherein:
   a) the sensor provided in said step of providing a sensor includes a noise detector, and the preset normal vehicle driving condition includes a preset noise level.

8. A method as in claim 7, wherein:
   a) said noise detector includes a human voice detector.

9. A method as in claim 1, wherein:
   a) the sensor provided in said step of providing a sensor includes at least two of an accelerometer, an engine rpm sensor, a speed sensor, a sound-actuated sensor, a brake-usage sensor, a horn-usage sensor, and a steering wheel-usage sensor; and
   b) the at least two sensors initiate the signal to provide a notice when each respective one of the at least two sensors detects a respective vehicle condition which exceeds a further predetermined value and which further predetermined value is less than or equal to a predetermined value corresponding to the preset normal vehicle driving condition.

10. A method as in claim 1, wherein:
    a) the further predetermined period of time selected so as to not anger the vehicle operator by giving the vehicle operator a negative stroke is not more than a few seconds.

11. A method as in claim 1, wherein:
    a) the notice includes a notice intervention; and
    b) said signal provides the notice intervention to the vehicle operator when said sensor detects the vehicle operating condition which exceeds the preset normal vehicle driving condition.

12. A method as in claim 1, wherein:
    a) the sensor provided in said step of providing a sensor includes an adjustment for varying a value of the preset normal vehicle driving condition.

13. A method as in claim 1, wherein:
a) said sensor includes a noise sensor which detects a noise level corresponding to yelling.

14. A method as in claim 1, wherein:
a) said signal provides a visual notice.

15. A method as in claim 1, wherein:
a) said signal provides an audible notice.

16. A method as in claim 1, wherein:
a) said sensor includes a sound-actuated sensor which detects a sound which exceeds a predetermined level.

17. A method as in claim 1, wherein:
a) said sensor includes a pressure-actuated sensor which detects a pressure which exceeds a predetermined level.

18. A method as in claim 17, wherein:
a) said pressure-actuated sensor is mounted on a steering wheel assembly of a vehicle.

19. A method as in claim 18, wherein:
a) said pressure-actuated sensor detects pressure on a steering wheel region of a steering wheel assembly of a vehicle.

20. A method as in claim 18, wherein:
a) said pressure-actuated sensor detects pressure on a horn region of a steering wheel assembly of a vehicle.

21. A method as in claim 1, wherein:
a) an ignition sensor is provided, said ignition sensor determines a vehicle ON condition and a vehicle OFF condition;
b) said signal is operatively associated with said ignition sensor; and
c) said ignition sensor resets a deactivated signal after said ignition sensor determines a vehicle OFF condition followed by a vehicle ON condition.

22. A method as in claim 1, wherein:
a) said sensor includes an accelerometer.

23. A method as in claim 1, further comprising:
a) providing a computer, said computer being operatively associated with said sensor and said signal, and said computer monitors output from said sensor and governs activation and duration of said signal.

24. A method as in claim 1, further comprising:
a) providing a computer chip, the computer chip being operatively associated with said sensor and said signal, and said computer chip monitors output from said sensor and governs activation and duration of said signal.

25. A system for monitoring driver behavior for reducing aggressive driving behavior in a vehicle, comprising:
a) a driver behavior monitoring apparatus for monitoring and collecting driver behavior data;
b) an analyzing apparatus operatively associated with said driver behavior monitoring apparatus for analyzing the driver behavior data collected by said driver behavior monitoring apparatus;
c) a signal apparatus operatively associated with said driver behavior monitoring apparatus for providing a notice to a driver in a vehicle monitored by said driver behavior monitoring apparatus when the driver behavior data has a value exceeding a predetermined driver behavior data value; and
d) said analyzing apparatus causing said signal apparatus to discontinue providing the notice to a driver after a predetermined period of time in which the driver behavior data has a value exceeding a predetermined driver behavior data value, and whether or not the driver behavior data has a value exceeding the predetermined driver behavior data value after the predetermined period of time, and said analyzing apparatus prevents said signal apparatus from providing a further notice until after the vehicle in which a driver is being monitored has been turned off and on, so that the vehicle operator is not given a negative stroke.

26. A system as in claim 25, wherein:
a) the driver behavior monitoring apparatus monitors and collects driver voice data.

27. A system as in claim 25, wherein:
a) the driver behavior monitoring apparatus monitors and collects driver voice data corresponding to yelling.

28. A system as in claim 25, wherein:
a) said signal apparatus provides a visual warning.

29. A system as in claim 28, wherein:
a) the driver behavior monitoring apparatus monitors and collects driver horn-usage data.

30. A system as in claim 25, wherein:
a) said signal apparatus provides an audible warning.

31. A system as in claim 25, wherein:
a) the driver behavior data includes at least one of horn usage data, steering wheel gripping data, vehicle speed data, vehicle acceleration data, vehicle jerk data, vehicle braking data, and engine rpm data.

32. A method of reducing vehicle operator road rage, the method comprising:
a) monitoring vehicle operator data;
b) collecting vehicle operator data;
c) analyzing the monitored and collected vehicle operator data for determining vehicle operator behavior data;
d) giving the vehicle operator a positive stroke if the vehicle operator operates the vehicle for greater than a predetermined time without engaging in an aggressive driving behavior;
e) providing an intervention if the vehicle operator engages in an aggressive driving behavior;
f) stopping the intervention if the vehicle operator continues to engage in aggressive driving behavior for more than a few seconds; and
g) neither a positive stroke nor a negative stroke is provided to the vehicle operator until after a predetermined event has occurred.

33. A method as in claim 32, wherein:
a) the predetermined event includes a time greater than a predetermined period of time being exceeded.

34. A method as in claim 32, wherein:
a) the predetermined event includes a time free of aggressive driver behavior.

35. A method as in claim 32, wherein:
a) the predetermined event includes the vehicle having been through an OFF/ON condition.

* * * * *